(12) United States Patent
Ramin et al.

(10) Patent No.: US 6,367,484 B1
(45) Date of Patent: Apr. 9, 2002

(54) MAKE-UP METHOD FOR KERATINOUS MATERIAL

(75) Inventors: Roland Ramin, Paris; Ingrid Brenne, L'Hay-les-Roses, both of (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 09/582,794

(22) PCT Filed: Nov. 5, 1999

(86) PCT No.: PCT/FR99/02714

§ 371 Date: Aug. 9, 2000

§ 102(e) Date: Aug. 9, 2000

(87) PCT Pub. No.: WO00/27345

PCT Pub. Date: May 18, 2000

(30) Foreign Application Priority Data

Nov. 6, 1998 (FR) .............................. 98/14110

(51) Int. Cl.[7] .......................... A45D 24/00; A61K 7/06
(52) U.S. Cl. ........................................ 132/200; 132/209
(58) Field of Search .......................... 132/200, 202, 132/205, 209; 424/61; 106/5, 195, 6, 191

(56) References Cited

U.S. PATENT DOCUMENTS

| 3,875,950 A | 4/1975 | Gens |
| 4,158,053 A | 6/1979 | Greene et al. |
| 4,822,423 A | 4/1989 | Soyama et al. |
| 4,855,144 A * | 8/1989 | Leong et al. ................ 424/487 |
| 5,599,549 A * | 2/1997 | Wivell et al. ................ 424/401 |
| 5,824,666 A * | 10/1998 | Deckner et al. ............. 514/152 |
| 6,194,363 B1 * | 2/2001 | Murray ........................ 510/119 |

FOREIGN PATENT DOCUMENTS

| EP | 0 288 012 | 10/1988 |
| EP | 0 764 436 | 3/1997 |
| FR | 2 578 741 | 9/1986 |
| GB | 2 238 242 | 5/1991 |
| WO | WO 98/31329 | 7/1998 |

* cited by examiner

Primary Examiner—John J. Wilson
Assistant Examiner—Robyn Kieu Doan
(74) Attorney, Agent, or Firm—Finnegan, Henderson, Farabow, Garrett & Dunner, L.L.P.

(57) ABSTRACT

The invention relates to a process for making up keratin substances, which consists in applying to the keratin substances a first coat of a film-forming composition comprising a cosmetically acceptable medium and at least one film-forming polymer, followed by applying to at least a part of the first coat, and before the first coat has dried, a second coat consisting essentially of solid particles that are insoluble in the cosmetically acceptable medium of the composition, having a substantially spherical or ovoid shape and having a density ranging from 800 kg/m³ to 10,000 kg/m³.

Figure 1:
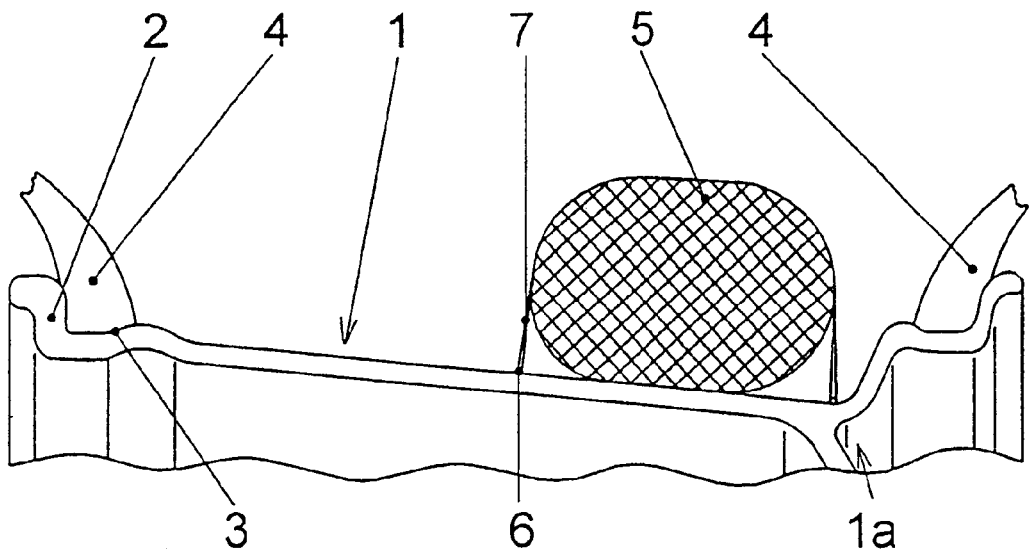
Figure 2:
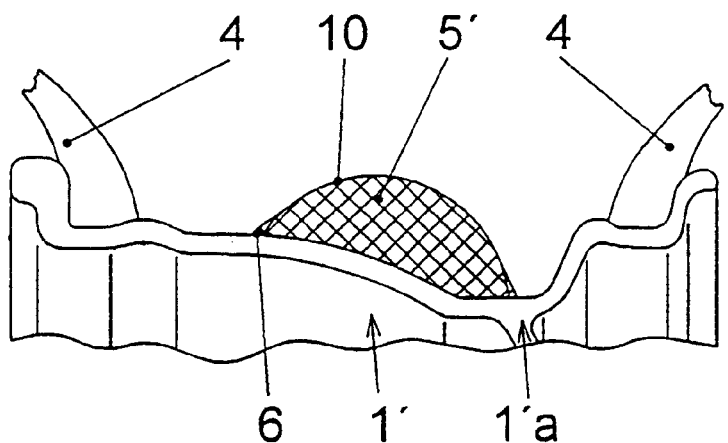
Figure 3:
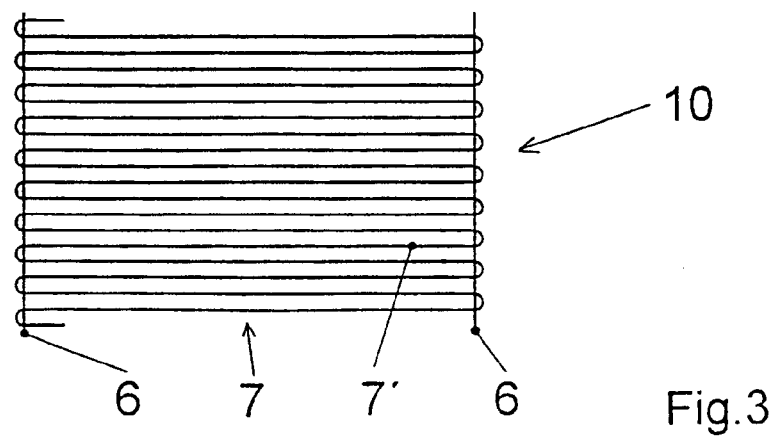
Figure 4:
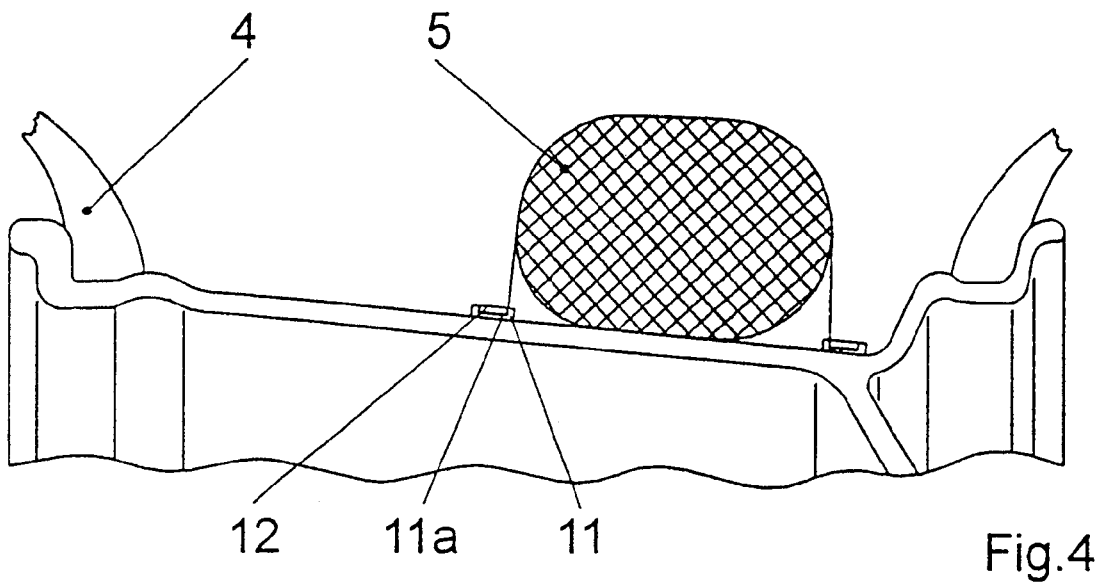
Figure 5:
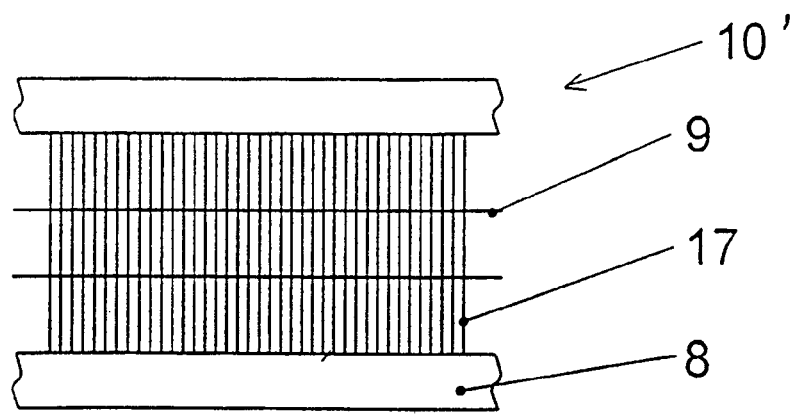
Figure 6:
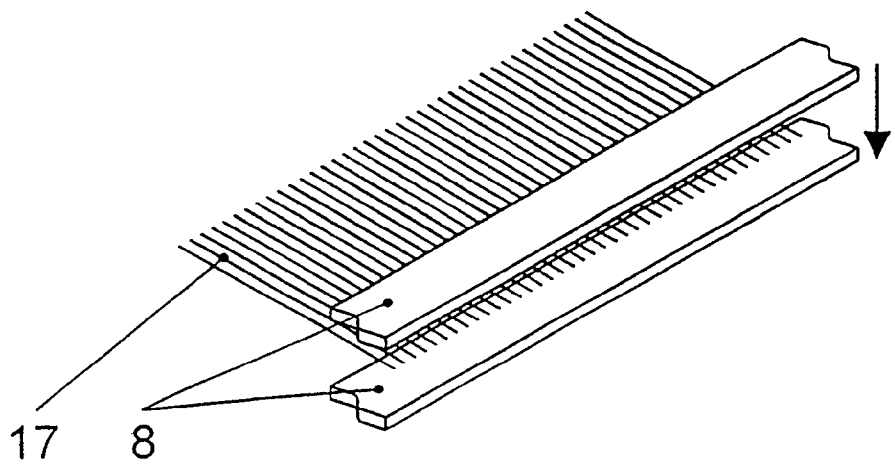
Figure 7:
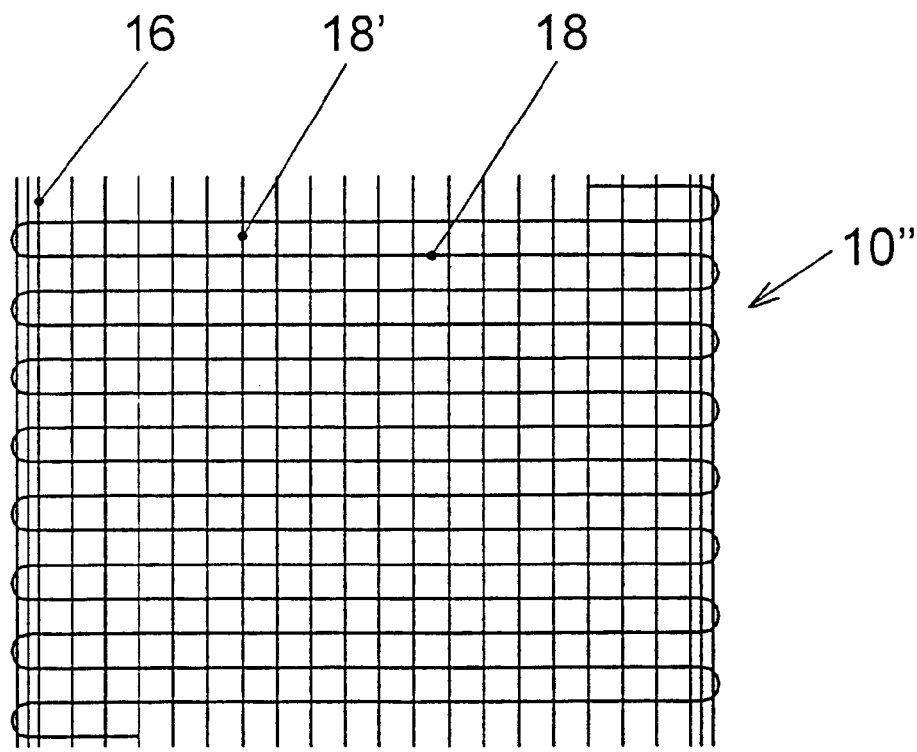
Figure 8:
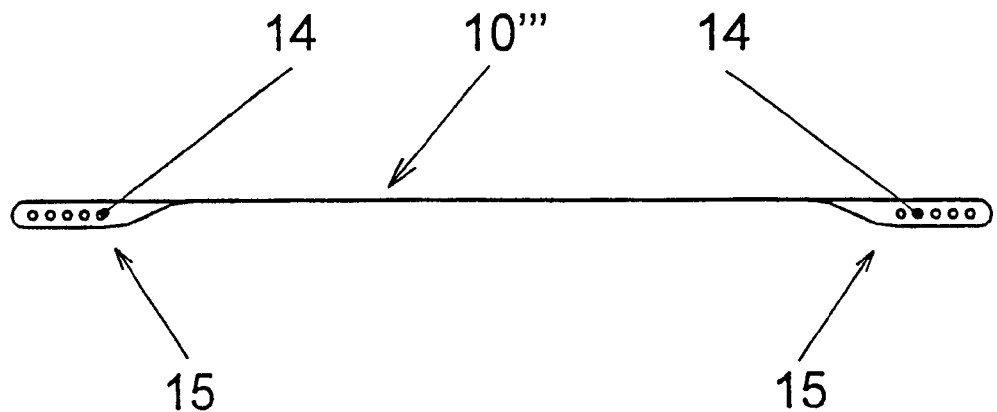

The invention also relates to a make-up kit comprising the film-forming composition and the solid particles.

70 Claims, 3 Drawing Sheets

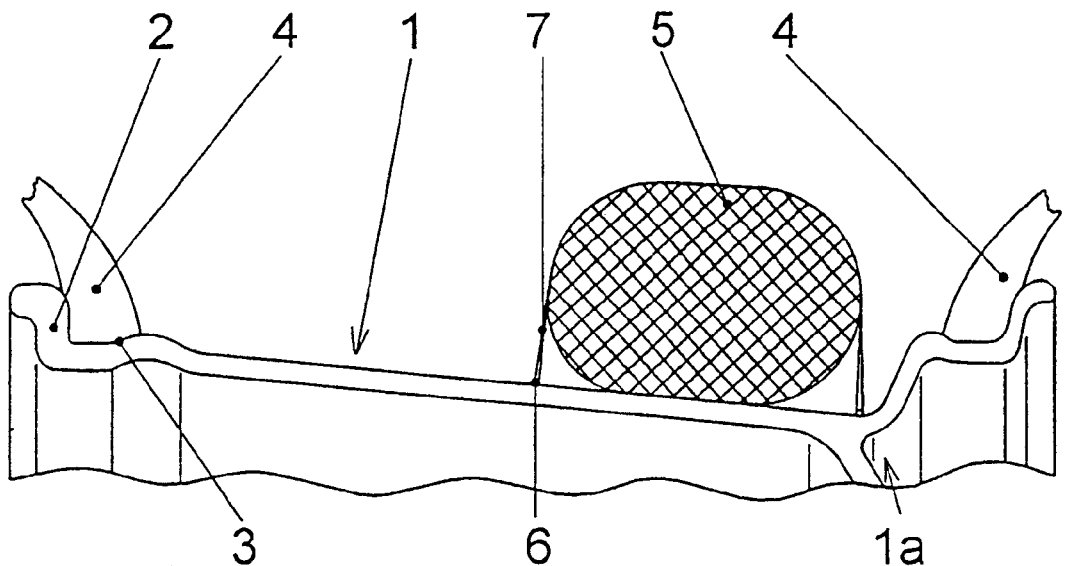

MAKE-UP METHOD FOR KERATINOUS MATERIAL

The present invention relates to a process for making up keratin substances, comprising the application to the keratin substances of a first coat of a film-forming composition and a second coat of solid particles. The invention also relates to a make-up kit for carrying out the process. The process according to the invention can be applied to the skin both of the face and of the body, to the lips and to superficial body growths such as the nails, the eyelashes, the eyebrows or the hair; this process is particularly suitable for making up the nails.

The film-forming composition can be a nail varnish, a face powder, an eyeshadow, a foundation, a make-up product for the lips or a make-up product for the body.

Nail varnish compositions generally comprise a film-forming polymer either dissolved in an organic solvent or dispersed in the form of particles in an aqueous medium. Such varnishes are described, for example, in documents U.S. Pat. No. 4,158,053 and FR-A-2 578 741.

After applying one or more coats of the composition to the nail and after drying, these nail varnishes generally lead to the formation of a smooth, continuous and homogeneous, glossy or matt film. Certain films also have good cosmetic properties such as good staying power and in particular good adhesion to the nail, and good resistance to water, to rubbing and to impacts.

With the change in fashion, more demanding consumers are looking for new make-up products which give original or specific make-up effects. There is thus a need to provide a make-up product whose application to a support such as the skin or the superficial body growths of human beings gives a make-up effect which is different from that of the continuous and homogeneous films currently obtained with the products available on the market.

The aim of the present invention is thus to provide a make-up composition for obtaining a relief make-up on the skin and on superficial body growths, while at the same time having good staying power over time.

The Applicant has found that a novel type of make-up for the skin and/or superficial body growths can be obtained using a specific process for applying a film-forming composition and solid particles. This process makes it possible to distribute and maintain at the surface particles more or less uniformly at the surface: an original relief make-up effect is thus obtained, giving volume and body to the keratin substances, for example the nails. In addition, the make-up has good adhesion to the made-up support and good staying power, in particular with respect to rubbing and impacts. Furthermore, the particles give the impression of the presence of bubbles at the surface of the make-up.

More specifically, a subject of the invention is a process for making up keratin substances, which consists in applying to the keratin substances a first coat of a first film-forming composition comprising a cosmetically acceptable medium and at least one first film-forming polymer, followed by applying to at least a part of the first coat, and before the first coat has dried, a second coat consisting essentially of solid particles that are insoluble in the cosmetically acceptable medium of the first composition and having a density ranging from 800 kg/m$^3$ to 10,000 kg/m$^3$, the solid particles having a substantially spherical or ovoid shape.

A subject of the invention is also a make-up kit comprising a first composition comprising at least one first film-forming polymer in a cosmetically acceptable medium, and solid particles having a substantially spherical or ovoid shape and having a density ranging from 800 kg/m$^3$ to 10,000 kg/m$^3$.

According to the invention, the second coat is applied at least to a part of the first coat, or even to all of the first coat, before the first coat has dried. It can be applied either to one of the ends of the first coat or to the middle, or alternatively in a discontinuous manner, in particular in the form of symmetrical or dissymmetrical geometric patterns (for example in the form of spots, squares, circles or stars), distributed randomly or in an ordered manner, along precise or vague contours.

In the process according to the invention, the second coat is obtained by direct application of the solid particles without them being mixed with a liquid medium, to allow good distribution on the surface of the first coat.

According to a first embodiment of the process of the invention, the second coat can be applied by sprinkling the solid particles onto the first coat before drying. The particles then come into contact with the first coat and become distributed more or less uniformly over the entire surface of the first coat. The excess of particles not in contact with the first coat do not become bound and are removed when the support thus made up is shaken or when the excess of particles is removed with a fine or coarse brush or with a puff of air. The sprinkling can advantageously be carried out through a screen or a stencil.

According to a second embodiment of the process according to the invention, the surface of the first coat applied to the keratin substances is placed in contact, before drying, directly with the solid particles stored, for example, in a container. In the case of a nail varnish, the fingers can be dipped directly into a finger dish.

The process according to the invention thus makes it possible to deposit and bind a quite homogeneous coat of solid particles which is of uniform thickness, thus giving an original relief make-up effect. Furthermore, the particles of substantially spherical or ovoid shape give the make-up a soft feel.

This two-layer architecture can be adapted to any make-up product for the skin not only for the face but also for the scalp and the body, for mucous membranes such as the lips, and for superficial body growths such as the nails. This architecture can also be applied to make-up accessories such as false nails, false eyelashes, wigs or to adhesive patches or disks on the skin or the lips (such as beauty spots).

It is possible to apply to the second coat of solid particles a third coat of a second film-forming composition comprising, in a cosmetically acceptable medium, a second film-forming polymer. This third coat makes it possible in particular to ensure very good staying power of the second coat on the first coat; it also makes it possible to provide colour shades, in particular when the colour of the third coat is different from the colour of the first coat and/or from the colour of the particles in the second coat.

The invention also relates to a made-up support whose make-up effect can be obtained by the process according to the invention.

Another subject of the invention is the use of the first composition and of the solid particles as defined above to obtain a make-up effect with surface relief, which has good staying power.

A subject of the invention is also the use of solid particles as defined above to obtain a make-up effect with surface relief, which has good staying power.

The Inventors have found, surprisingly, that the application of the solid particles in accordance with the process according to the invention makes it possible to obtain a make-up effect with uniform surface relief, which has good adhesion to the made-up support and good staying power in particular with respect to rubbing and to impacts. On the other hand, by adding the solid particles to a film-forming composition as defined above, the particles have a tendency to sediment out during storage of the composition, and it is difficult to obtain a uniform distribution of these particles in the film-forming composition. As a result, the application of this mixture, for example using a fine brush, is made difficult on account of the heterogeneity of the mixture and this application does not give a uniform distribution of the particles deposited onto the support to be treated. Thus, the process according to the invention makes it possible to obtain a make-up effect with homogeneous relief comprising a uniform distribution of the solid particles. This process allows the first coat to be covered, to the point of saturation, and allows a coat of constant thickness of particles to be formed.

The solid particles used in the process according to the invention have a density ranging from 800 kg/m$^3$ to 10,000 kg/m$^3$ (0.8 to 10 g/cm$^3$), preferably from 1000 kg/m$^3$ to 3000 kg/m$^3$ (1 to 3 g/cm$^3$) and better still from 2300 to 3000 kg/m$^3$ (2.3 to 3 g/cm$^3$), to allow good contact with the first coat before drying and thus to obtain good staying power of the particles after the first coat has dried.

Advantageously, the solid particles have a substantially spherical shape, to allow them to be distributed satisfactorily when they are applied to the first coat.

The solid particles used in the process according to the invention can have an average size ranging from 2.5 μm to 5 mm and better still from 50 μm to 2 mm. The smaller the size of the particles, the greater the staying power of the particles on the first coat; these particles also make it possible to produce finer and more intricate designs, in particular using a stencil.

The solid particles can be made of any material which satisfies the density properties defined above. For example, the solid particles can be made of a material chosen from glass, zirconium oxide, tungsten carbide, plastics such as polyurethanes, polyamides, polytetrafluoroethylene or polypropylene, metals such as steel, copper, brass or chromium, wood, marble, onyx, jade, natural mother-of-pearl, precious stones (diamond, emerald, ruby or sapphire), amethyst or aquamarine. Glass beads are preferably used, such as those sold under the name "Silibeads®" by the company Sigmund Lindner; these beads give the make-up gloss and sparkle.

The solid, deformable or non-deformable particles can be solid or hollow, colourless or coloured and coated or uncoated.

According to the process of the invention, the cosmetically acceptable medium of the first and second compositions can comprise, independently of each other, an aqueous medium or an organic-solvent medium.

Among the film-forming polymers which can be used in the composition for the process of the present invention, mention may be made of synthetic polymers, of radical-mediated type or of polycondensate type, polymers of natural origin and mixtures thereof.

The expression "radical-mediated film-forming polymer" means a polymer obtained by polymerization of monomers containing unsaturation, in particular ethylenic unsaturation, each monomer being capable of homopolymerizing (in contrast with polycondensates).

The film-forming polymers of radical-mediated type can be, in particular, vinyl polymers or copolymers, in particular acrylic polymers.

The vinyl film-forming polymers can result from the polymerization of monomers containing ethylenic unsaturation having at least one acid group and/or esters of these acidic monomers and/or amides of these acidic monomers.

Anionic radical-mediated film-forming polymers are preferably used, i.e. polymers containing at least one monomer with an acid group.

α,β-Ethylenic unsaturated carboxylic acids such as acrylic acid, methacrylic acid, crotonic acid, maleic acid or itaconic acid, can be used as monomers bearing an acid group. (Meth)acrylic acid and crotonic acid are preferably used, and more preferably (meth)acrylic acid.

The esters of acidic monomers are advantageously chosen from the esters of (meth)acrylic acid (also referred to as (meth)acrylates), especially (meth)acrylates of an alkyl, in particular of a $C_1$–$C_{20}$ alkyl, preferably a $C_1$–$C_8$ alkyl, (meth)acrylates of an aryl, in particular of a $C_6$–$C_{10}$ aryl, and (meth)acrylates of a hydroxyalkyl, in particular of a $C_2$–$C_6$ hydroxyalkyl.

Among the alkyl (meth)acrylates which may be mentioned are methyl methacrylate, ethyl methacrylate, butyl methacrylate, isobutyl methacrylate, 2-ethylhexyl methacrylate and lauryl methacrylate.

Among the hydroxyalkyl (meth)acrylates which may be mentioned are hydroxyethyl acrylate, 2-hydroxypropyl acrylate, hydroxyethyl methacrylate and 2-hydroxypropyl methacrylate.

Among the aryl (meth)acrylates which may be mentioned are benzyl acrylate and phenyl acrylate.

The (meth)acrylic acid esters which are particularly preferred are the alkyl (meth)acrylates.

According to the present invention, the alkyl group of the esters can be either fluorinated or perfluorinated, i.e. some or all of the hydrogen atoms in the alkyl group are substituted with fluorine atoms.

As amides of the acidic monomers, mention may be made, for example, of (meth)acrylamides, and especially N-alkyl (meth)acrylamides, in particular of a $C_2$–$C_{12}$ alkyl. Among the N-alkyl (meth)acrylamides which may be mentioned are N-ethylacrylamide, N-t-butylacrylamide and N-t-octylacrylamide.

The vinyl film-forming polymers can also result from the homopolymerization or copolymerization of at least one monomer chosen from vinyl esters and styrene monomers. In particular, these monomers can be polymerized with acidic monomers and/or esters thereof and/or amides thereof, such as those mentioned above.

As examples of vinyl esters, mention may be made of vinyl acetate, vinyl neodecanoate, vinyl pivalate, vinyl benzoate and vinyl t-butylbenzoate.

As styrene monomers, mention may be made of styrene and alpha-methylstyrene.

The list of monomers given is not limiting and it is possible to use any monomer known to those skilled in the art which falls within the categories of acrylic and vinyl monomers (including monomers modified with a silicone chain).

As acrylic film-forming polymers in aqueous dispersion which can be used according to the invention, mention may be made of those sold under the names Neocryl XK-90®, Neocryl A-1070®, Neocryl A-1090®, Neocryl BT-62®, Neocryl A-1079® and Neocryl A-523® by the company Zeneca and Dow Latex 432® by the company Dow Chemical.

Among the polycondensates which can be used as film-forming polymers, mention may thus be made of anionic, cationic, nonionic or amphoteric polyurethanes, polyurethane-acrylics, polyurethane-polyvinylpyrrolidones, polyester-polyurethanes, polyether-polyurethanes, polyureas, polyurea-polyurethanes and mixtures thereof.

The film-forming polyurethane can be, for example, an aliphatic, cycloaliphatic or aromatic polyurethane, polyurea-urethane or polyurea copolymer, comprising, alone or as a mixture:

at least one sequence of aliphatic and/or cycloaliphatic and/or aromatic polyester origin, and/or at least one branched or unbranched silicone sequence, for example polydimethylsiloxane or polymethylphenylsiloxane, and/or at least one sequence comprising fluoro groups.

As polyurethane film-forming polymer in aqueous dispersion which can be used according to the invention, mention may be made in particular of the polyester-polyurethanes sold under the names "Avalure UR-405®", "Avalure UR-410®", "Avalure UR-425®" and "Sancure 2060®" by the company Goodrich and the polyether-polyurethanes sold under the names "Sancure 878®" by the company Goodrich and "Neorez R 970®" by the company ICI.

Among the film-forming polycondensates which can also be mentioned are polyesters, polyesteramides, fatty-chain polyesters, polyamides and epoxy ester resins, resins resulting from the condensation of formaldehyde with an arylsulphonamide, and arylsulphonamide epoxy resins.

The polyesters can be obtained, in a known manner, by polycondensation of dicarboxylic acids with polyols, in particular diols.

The dicarboxylic acids can be aliphatic, alicyclic or aromatic. Examples of such acids which may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecane-dioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acid monomers can be used alone or in combination with at least two dicarboxylic acid monomers. Among these monomers, phthalic acid, isophthalic acid or terephthalic acid is preferably chosen.

The diol can be chosen from aliphatic, alicyclic and aromatic diols. The diol preferably used is chosen from: ethylene glycol, diethylene glycol, triethylene glycol, 1,3-propanediol, cyclohexanedimethanol and 4-butanediol. Other polyols which can be used are glycerol, pentaerythritol, sorbitol and trimethylolpropane.

The polyesteramides can be obtained in a similar manner to the polyesters, by polycondensation of diacids with diamines or with amino alcohols. Diamines which can be used are ethylenediamine, hexamethylenediamine, and meta- or para-phenylene-diamine. An amino alcohol which can be used is monoethanolamine.

The polyester can also comprise at least one monomer bearing at least one group —$SO_3M$, with M representing a hydrogen atom, an ammonium ion $NH_4^+$ or a metal ion such as, for example, an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ can be used in particular.

The aromatic nucleus of the difunctional aromatic monomer also bearing a group —$SO_3M$ as described above can be chosen, for example, from benzene, naphthalene, anthracene, diphenyl, oxydiphenyl, sulphonyldiphenyl and methylenediphenyl nuclei. Examples of difunctional aromatic monomers also bearing a group —$SO_3M$ which may be mentioned are: sulphoisophthalic acid, sulphotereph-thalic acid, sulphophthalic acid and 4-sulphonaphthalene-2,7-dicarboxylic acid.

Copolymers based on isophthalate/sulphoisophthalate, and more particularly copolymers obtained by condensation of di-ethylene glycol, cyclohexanedimethanol, isophthalic acid and sulphoisophthalic acid, are preferably used in the compositions forming the subject of the invention. Such polymers are sold, for example, under the brand name Eastman AQ by the company Eastman Chemical Products.

The polymers of natural origin, optionally modified, can be chosen from shellac resin, sandarac gum, dammar resins, elemi gums, copal resins, cellulose polymers such as nitrocellulose, cellulose acetate, cellulose acetobutyrate, cellulose acetopropionate, ethylcellulose and mixtures thereof.

The first and/or second film-forming polymers can be dissolved or dispersed in the form of particles in the corresponding cosmetically acceptable medium for each composition according to the invention. The first and the second film-forming polymer can generally be present, respectively, in a content ranging from 1% to 70% by weight, relative to the total weight of the first and second composition, respectively, and better still ranging from 10% to 40% by weight.

As organic solvents which can be used in the invention, mention may be made of:

ketones that are liquid at room temperature, such as methyl ethyl ketone, methyl isobutyl ketone, diisobutyl ketone, isophorone, cyclohexanone and acetone;

alcohols that are liquid at room temperature, such as ethanol, isopropanol, diacetone alcohol, 2-butoxy-ethanol and cyclohexanol;

glycols that are liquid at room temperature, such as ethylene glycol, propylene glycol, pentylene glycol and glycerol;

propylene glycol ethers that are liquid at room temperature, such as propylene glycol monomethyl ether, propylene glycol monomethyl ether acetate and dipropylene glycol mono-n-butyl ether;

short-chain esters (containing from 3 to 8 carbon atoms in total), such as ethyl acetate, methyl acetate, propyl acetate, n-butyl acetate and isopentyl acetate;

ethers that are liquid at room temperature, such as diethyl ether, dimethyl ether or dichlorodiethyl ether;

alkanes that are liquid at room temperature, such as decane, heptane, dodecane and cyclohexane;

cyclic aromatic compounds that are liquid at room temperature, such as toluene and xylene;

aldehydes that are liquid at room temperature, such as benzaldehyde and acetaldehyde;

mixtures thereof.

These solvents are more particularly suitable for nail make-up: the composition thus constitutes a nail varnish.

In each composition containing an organic-solvent medium, the organic solvent can be present in a content ranging from 30 to 99% by weight, relative to the total weight of each composition, and preferably from 60% to 90% by weight.

When the compositions for carrying out the process according to the invention contain an aqueous medium, this medium can consist essentially of water or of an aqueous-alcoholic mixture in particular containing $C_1$–$C_5$ lower monoalcohols. The water content in each composition containing an aqueous medium can range from 30 to 99% by weight, relative to the total weight of each composition, and preferably from 60% to 90% by weight.

To improve the film-forming properties of the first and/or of the second composition in the process according to the invention, the first and the second compositions can comprise an additional film-forming agent.

Such an additional film-forming agent can be chosen from any compound known to those skilled in the art as being capable of fulfilling the desired function, and can be chosen in particular from plasticizers.

In addition, when one of the compositions for carrying out the process according to the invention comprises a film-forming polymer in the form of particles dispersed in the medium of the composition, the additional film-forming agent can also be chosen from coalescers.

Each composition in the process according to the invention can also comprise any additive known to those skilled in the art as being capable of being incorporated into such a composition, such as thickeners, spreading agents, wetting agents, dispersing agents, anti-foaming agents, preserving agents, UV screening agents, dyes, pigments, active agents, surfactants, moisturizers, fragrances, neutralizing agents, stabilizers and antioxidants. Needless to say, a person skilled in the art will take care to select this or these optional additional compound(s), and/or the amount thereof, such that the advantageous properties of the composition according to the invention are not, or are not substantially, adversely affected by the addition envisaged.

Each composition according to the invention can be prepared by a person skilled in the art on the basis of his general knowledge and according to the state of the art.

Advantageously, the first and second compositions of the process according to the invention are packaged in separate compartments or containers, accompanied by suitable, identical or different application means, such as fine or coarse brushes, feathers and sponges.

The invention is illustrated in greater detail in the examples which follow.

EXAMPLE 1

A nail varnish having the composition below was prepared:

| | |
|---|---|
| Nitrocellulose | 10.9% |
| Toluene sulphonamide formaldehyde resin (Ketjenflex MS80 sold by Akzo) | 10.7% |
| Tributyl acetyl citrate | 6.5% |
| Toluene | 31.0% |
| Butyl acetate | 22.6% |
| Ethyl acetate | 9.3% |
| Isopropyl alcohol | 7.7% |
| Stearalkonium hectorite | 1.3% |
| Citric acid | 0.1% |

A first coat of this nail varnish was applied to the nails, after which glass microbeads sold under the name "Silibeads" art. 4500 by the company Sigmund (density=2500 kg/m$^3$; particle size from 0.3 to 0.4 mm approximately) were sprinkled onto this coat before drying. After drying the first coat, the microbeads in contact are fixed and distributed homogeneously at the surface of the nail; the excess of beads is removed by shaking the fingers. From 800 to 1000 beads per cm$^2$ approximately are thus deposited.

A make-up effect with relief, which has good staying power, in particular good wear strength and a soft feel, is thus obtained on the nails; furthermore, the beads reflect light and give a sparkling, glossy effect.

To reinforce the staying power of the make-up, a third finishing coat having the composition below can be applied over the particles:

| | |
|---|---|
| Nitrocellulose | 15 g |
| Plasticizer | 6 g |
| Solvents (butyl acetate, ethyl acetate) | qs 100 g |

EXAMPLE 2

A nail varnish having the composition below as prepared:

| | |
|---|---|
| Dispersion of acrylic polymer (40% solids) | 38 g |
| Dispersion of polyurethane (30% solids) | 50 g |
| Colloidal silicic acid (Aerosil MOX80) | 0.7 g |
| Additives (dyes, active agents) | 1.3 g |
| Water qs | 100 g |

A first coat of this nail varnish was applied to the nails, after which steel beads having a density=7900 kg/m$^3$ and a particle size of about 2 mm were sprinkled onto this coat before drying. After drying the first coat, the microbeads in contact are fixed and distributed homogeneously at the surface of the nail; the excess of beads is removed by shaking the fingers.

A make-up effect with relief, which has good staying power, in particular good wear strength and a soft feel, is thus obtained on the nails.

EXAMPLE 3

A nail varnish having the composition below was prepared:

| | |
|---|---|
| Film-forming polymers (nitrocellulose, resin) | 28 g |
| Plasticizer | 7 g |
| Isopropyl alcohol | 5 g |
| Ethylated guar with a degree of substitution of about 2.5 (1) | 3 g |
| Pigments | 1 g |
| Ethyl acetate/butyl acetate qs | 100 g |

(1) sold under the name N-Hance AG 200 ® by Aqualon

A first coat of this nail varnish was applied to the nails, after which Nylon powder sold under the name "Orgasol D 2002 Nat Cos" by the company Atochem (density=1020 kg/m$^3$; particle size of approximately 20 µm) was sprinkled onto this coat before drying. After drying the first coat, the particles in contact are fixed and distributed homogeneously at the surface of the nail; the excess of particles is removed by shaking the fingers.

A make-up effect with relief, which has a soft feel, is thus obtained.

What is claimed is:

1. A process for making up a keratin substance, comprising:

applying to a keratin substance a first coat comprising a first film-forming composition comprising a cosmetically acceptable medium and at least one first film-forming polymer; and applying to at least a part of said first coat, and before said first coat has dried, a second coat comprising solid particles, wherein said solid particles are insoluble in the cosmetically acceptable medium of said first film-forming composition, have a density ranging from 800 kg/m$^3$ to 10,000 kg/m$^3$, and have a substantially spherical or ovoid shape.

2. A process according to claim 1, wherein said solid particles have a density ranging from 1000 kg/m$^3$ to 3000 kg/m$^3$.

3. A process according to claim 2, wherein said solid particles have a density ranging from 2300 kg/m$^3$ to 3000 kg/m$^3$.

4. A process according to claim 1, wherein said solid particles have a size ranging from 2.5 μm to 5 mm.

5. A process according to claim 4, wherein said solid particles have a size ranging from 50 μm to 2 mm.

6. A process according to claim 1, wherein said solid particles have a substantially spherical shape.

7. A process according to claim 1, wherein said solid particles comprise a material chosen from glass, zirconium oxide, tungsten carbide, polyurethanes, polyamides, polytetrafluoroethylene, polypropylene, metals, wood, marble, onyx, jade, natural mother-of-pearl, precious stones, amethyst, and aquamarine.

8. A process according to claim 7, wherein said metals are chosen from steel, copper, brass, and chromium.

9. A process according to claim 1, wherein said solid particles are glass microbeads.

10. A process according to claim 1, further comprising applying to said second coat, a third coat comprising a second film-forming composition comprising a cosmetically acceptable medium and at least one second film-forming polymer, wherein said at least one second film-forming polymer can be the same as said at least one first film-forming polymer.

11. A process according to claim 1, wherein said first film-forming composition comprises a solvent medium.

12. A process according to claim 1, wherein said at least one first film-forming polymer is dissolved or dispersed in the form of particles in said cosmetically acceptable medium.

13. A process according to claim 1, wherein said at least one first film-forming polymer is chosen from radical-mediated polymers, polycondensates, and polymers of natural origin.

14. A process according to claim 1, wherein said at least one first film-forming polymer is chosen from vinyl polymers, polyurethanes, polyesters, and cellulose polymers.

15. A process according to claim 1, wherein the amount of said at least one first film-forming polymer ranges from 1% to 70% by weight relative to the total weight of said first film-forming composition.

16. A process according to claim 15, wherein the amount of said at least one first film-forming polymer ranges from 10% to 40% by weight relative to the total weight of said first film-forming composition.

17. A process according to claim 1, wherein said first film-forming composition further comprises at least one additive chosen from additional film-forming agents, thickeners, spreading agents, wetting agents, dispersing agents, anti-foaming agents, preserving agents, UV screening agents, dyes, pigments, active agents, surfactants, moisturizers, fragrances, neutralizing agents, stabilizers, and antioxidants.

18. A process according to claim 17, wherein said additional film-forming agents are present in an amount ranging from 0.5% to 20% by weight relative to the total weight of said first film-forming composition.

19. A process according to claim 18, wherein said additional film-forming agents are present in an amount ranging from 2 to 10% by weight relative to the total weight of said first film-forming composition.

20. A process according to claim 1, wherein said first film-forming composition is in the form of a nail varnish, a face powder, an eyeshadow, a foundation, or a make-up product for the lips or the body.

21. A process according to claim 10, wherein said second film-forming composition comprises a solvent medium.

22. A process according to claim 10, wherein said at least one second film-forming polymer is dissolved or dispersed in the form of particles in said cosmetically acceptable medium.

23. A process according to claim 10, wherein said at least one second film-forming polymer is chosen from radical-mediated polymers, polycondensates, and polymers of natural origin.

24. A process according to claim 10, wherein said at least one second film-forming polymer is chosen from vinyl polymers, polyurethanes, polyesters, and cellulose polymers.

25. A process according to claim 10, wherein the amount of said at least one second film-forming polymer ranges from 1% to 70% by weight relative to the total weight of said second film-forming composition.

26. A process according to claim 25, wherein the amount of said at least one second film-forming polymer ranges from 10% to 40% by weight relative to the total weight of said second film-forming composition.

27. A process according to claim 10, wherein said second film-forming composition further comprises at least one additive chosen from additional film-forming agents, thickeners, spreading agents, wetting agents, dispersing agents, anti-foaming agents, preserving agents, UV screening agents, dyes, pigments, active agents, surfactants, moisturizers, fragrances, neutralizing agents, stabilizers and antioxidants.

28. A process according to claim 27, wherein said additional film-forming agents are present in an amount ranging from 0.5% to 20% by weight relative to the total weight of said second film-forming composition.

29. A process according to claim 28, wherein said additional film-forming agents are present in an amount ranging from 2 to 10% by weight relative to the total weight of said second film-forming composition.

30. A process according to claim 10, wherein said second film-forming composition is in the form of a nail varnish, a face powder, an eyeshadow, a foundation, or a make-up product for the lips or the body.

31. A process according to claim 1, wherein said second coat is deposited on said first coat by sprinkling said solid particles onto the first coat.

32. A process according to claim 1, wherein said second coat is deposited on said first coat by contact of the first coat with said solid particles.

33. A make-up product for a keratin substance, wherein said make-up product is obtained by:
    applying to a keratin substance a first coat comprising a first film-forming composition comprising a cosmetically acceptable medium and at least one first film-forming polymer; and
    applying to at least a part of said first coat, and before said first coat has dried, a second coat comprising solid particles, wherein said solid particles are insoluble in the cosmetically acceptable medium of said first film-forming composition, have a density ranging from 800 kg/m$^3$ to 10,000 kg/m$^3$, and have a substantially spherical or ovoid shape.

34. A make-up product according to claim 33, wherein a third coat comprising a second film-forming composition comprising a cosmetically acceptable medium and at least one second film-forming polymer is applied to said second coat, wherein said at least one second film-forming polymer can be the same as said at least one first film-forming polymer.

35. A make-up product according to claim 33, wherein said make-up product is used to obtain a make-up effect with surface relief and that has good staying power.

36. A make-up kit comprising:
a first film-forming composition comprising at least one first film-forming polymer in a cosmetically acceptable medium; and
solid particles having a substantially spherical or ovoid shape and having a density ranging from 800 kg/m$^3$ to 10,000 kg/m$^3$.

37. A make-up kit according to claim 36, wherein said solid particles have a size ranging from 2.5 µm to 5 mm.

38. A make-up kit according to claim 36, wherein said solid particles have a substantially spherical shape.

39. A make-up kit according to claim 36, wherein said make-up kit further comprises a second film-forming composition comprising at least one second film-forming polymer in a cosmetically acceptable medium, wherein said at least one second film-forming polymer can be the same as said at least one first film-forming polymer.

40. A make-up kit according to claim 36, wherein said first film-forming composition comprises a solvent medium.

41. A make-up kit according to claim 36, wherein said at least one first film-forming polymer is dissolved or dispersed in the form of particles in said cosmetically acceptable medium.

42. A make-up kit according to claim 36, wherein said at least one first film-forming polymer is chosen from radical-mediated polymers, polycondensates, and polymers of synthetic origin.

43. A make-up kit according to claim 36, wherein said at least one first film-forming polymer is chosen from vinyl polymers, polyurethanes, polyesters, and cellulose polymers.

44. A make-up kit according to claim 36, wherein the amount of said at least one first film-forming polymer ranges from 1% to 70% by weight relative to the total weight of said first film-forming composition.

45. A make-up kit according to claim 44, wherein the amount of said at least one first film-forming polymer ranges from 10% to 40% by weight relative to the total weight of said first film-forming composition.

46. A make-up kit according to claim 36, wherein said first film-forming composition further comprises at least one additive chosen from additional film-forming agents, thickeners, spreading agents, wetting agents, dispersing agents, anti-foaming agents, preserving agents, UV screening agents, dyes, pigments, active agents, surfactants, moisturizers, fragrances, neutralizing agents, stabilizers, and antioxidants.

47. A make-up kit according to claim 46, wherein said additional film-forming agents are present in an amount ranging from 0.5% to 20% by weight relative to the total weight of said first film-forming composition.

48. A make-up kit according to claim 47, wherein said additional film-forming agents are present in an amount ranging from 2% to 10% by weight relative to the total weight of said first film-forming composition.

49. A make-up kit according to claim 36, wherein said first film-forming composition is in the form of a nail varnish, a face powder, an eyeshadow, a foundation, or a make-up product for the lips or the body.

50. A make-up kit according to claim 36, wherein said make-up kit further comprises a means for applying said first film-forming composition to said keratin substance.

51. A make-up kit according to claim 50, wherein said means are chosen from fine and coarse brushes, feathers, and sponges.

52. A make-up kit according to claim 36, wherein said first film-forming composition and said solid particles are packaged in separate compartments or containers.

53. A make-up kit according to claim 39, wherein said second film-forming composition comprises a solvent medium.

54. A make-up kit according to claim 39, wherein said at least one second film-forming polymer is dissolved or dispersed in the form of particles in said cosmetically acceptable medium.

55. A make-up kit according to claim 39, wherein said at least one second film-forming polymer is chosen from radical-mediated polymers, polycondensates, and polymers of synthetic origin.

56. A make-up kit according to claim 39, wherein said at least one second film-forming polymer is chosen from vinyl polymers, polyurethanes, polyesters, and cellulose polymers.

57. A make-up kit according to claim 39, wherein the amount of said at least one second film-forming polymer ranges from 1% to 70% by weight relative to the total weight of said second film-forming composition.

58. A make-up kit according to claim 57, wherein the amount of said at least one second film-forming polymer ranges from 10% to 40% by weight relative to the total weight of said second film-forming composition.

59. A make-up kit according to claim 39, wherein said second film-forming composition further comprises at least one additive chosen from additional film-forming agents, thickeners, spreading agents, wetting agents, dispersing agents, anti-foaming agents, preserving agents, UV screening agents, dyes, pigments, active agents, surfactants, moisturizers, fragrances, neutralizing agents, stabilizers, and antioxidants.

60. A make-up kit according to claim 59, wherein said additional film-forming agents are present in an amount ranging from 0.5% to 20% by weight relative to the total weight of said second film-forming composition.

61. A make-up kit according to claim 60, wherein said additional film-forming agents are present in an amount ranging from 2% to 10% by weight relative to the total weight of said second film-forming composition.

62. A make-up kit according to claim 39, wherein said second film-forming composition is in the form of a nail varnish, a face powder, an eyeshadow, a foundation, or a make-up product for the lips or the body.

63. A make-up kit according to claim 39, wherein said make-up kit further comprises a means for applying said second film-forming composition to the keratin substance.

64. A make-up kit according to claim 63, wherein said means are chosen from fine and coarse brushes, feathers, and sponges.

65. A make-up kit according to claim 39, wherein said first film-forming composition, said second film-forming composition, and said solid particles are packaged in separate compartments or containers.

66. A make-up support comprising a make-up obtained by:
applying to a make-up support a first coat comprising a first film-forming composition comprising a cosmetically acceptable medium and at least one first film-forming polymer; and applying to at least a part of said first coat, and before said first coat has dried, a second coat comprising solid particles, wherein said solid particles are insoluble in the cosmetically acceptable medium of said first film-forming composition, have a density ranging from 800 kg/m$^3$ to 10,000 kg/m$^3$, and have a substantially spherical or ovoid shape.

67. A make-up support according to claim 66, wherein a third coat comprising a second film-forming composition comprising a cosmetically acceptable medium and at least one second film-forming polymer is applied to said second coat, wherein said at least one second film-forming polymer can be the same as said at least one first film-forming polymer.

68. A make-up support according to claim 66, wherein said make-up support is in the form of false nails.

69. A process of making a make-up product comprising:
including in a first compartment a first film-forming composition comprising a cosmetically acceptable medium and at least one first film-forming polymer, and including in a second compartment solid particles, wherein said solid particles are insoluble in the cosmetically acceptable medium of said first film-forming composition, have a density ranging from 800 kg/m$^3$ to 10,000 kg/m$^3$, and have a substantially spherical or ovoid shape.

70. A process for obtaining a make-up effect with surface relief and/or improved staying power comprising:
applying to a make-up support a first coat comprising a first film-forming composition comprising a cosmetically acceptable medium and at least one first film-forming polymer, and applying to at least a part of said first coat, and before said first coat has dried, a second coat comprising solid particles, wherein said solid particles are insoluble in the cosmetically acceptable medium of said first film-forming composition, have a density ranging from 800 kg/m$^3$ to 10,000 kg/m$^3$, and have a substantially spherical or ovoid shape.

* * * * *

UNITED STATES PATENT AND TRADEMARK OFFICE
CERTIFICATE OF CORRECTION

PATENT NO. : 6,367,484 B1
DATED : April 9, 2002
INVENTOR(S) : Roland Ramin et al.

It is certified that error appears in the above-identified patent and that said Letters Patent is hereby corrected as shown below:

<u>Title page,</u>
"70 Claims, 3 Drawing Sheets" should be -- 70 claims, No Drawing Sheets --.

<u>Drawings,</u>
Sheets 1 of 3, 2 of 3 and 3 of 3, should be deleted.

Signed and Sealed this

Tenth Day of September, 2002

Attest:

Attesting Officer

JAMES E. ROGAN
*Director of the United States Patent and Trademark Office*